United States Patent [19]

Morman et al.

[11] 4,125,113
[45] Nov. 14, 1978

[54] APPLICATOR FOR INSERTING HYGIENIC MEDIA INTO BODY CAVITIES

[75] Inventors: Raymond A. Morman, Butte Des Morts, Wis.; David V. Duchane, Ann Arbor, Mich.

[73] Assignee: Kimberly-Clark Corporation, Neenah, Wis.

[21] Appl. No.: 539,694

[22] Filed: Jan. 9, 1975

[51] Int. Cl.$^2$ .............................................. A61M 7/00
[52] U.S. Cl. ............................... 128/260; 128/218 P; 128/220
[58] Field of Search ............ 128/263, 224, 215, 218 R, 128/216, 218 P, 218 A, 218 PC, 234, 220, 260

[56] References Cited

U.S. PATENT DOCUMENTS

| | | | |
|---|---|---|---|
| 1,319,243 | 10/1919 | Powers | 128/215 |
| 2,002,024 | 5/1934 | Wood | 128/218 PA |
| 2,512,882 | 6/1950 | Truesdale | 128/215 |
| 2,607,343 | 8/1952 | Sarver | 128/218 C |
| 2,666,434 | 1/1954 | Ogle | 128/218 P |
| 2,972,991 | 2/1961 | Burke | 128/218 P |
| 3,492,876 | 2/1970 | Bull et al. | 128/218 R X |
| 3,753,437 | 8/1973 | Hood | 128/263 |
| 3,830,236 | 8/1974 | Hanke | 128/263 |

*Primary Examiner*—John D. Yasko
*Attorney, Agent, or Firm*—Daniel J. Hanlon, Jr.; William D. Herrick; Raymond J. Miller

[57] ABSTRACT

An improvement in tubular applicators for inserting hygienic media into body cavities. The applicator is of the type having telescoping elements in which annular flanges are disposed at the rear of each element and in which the rear surface of one flange confronts the front surface of the other flange. The improvement comprises providing a stop means on one or both of the confronting flange faces to keep the faces from touching when the elements are fully telescoped together and thus prevent entrapment of body tissue or hair between the closed flanges.

7 Claims, 6 Drawing Figures

U.S. Patent   Nov. 14, 1978   4,125,113
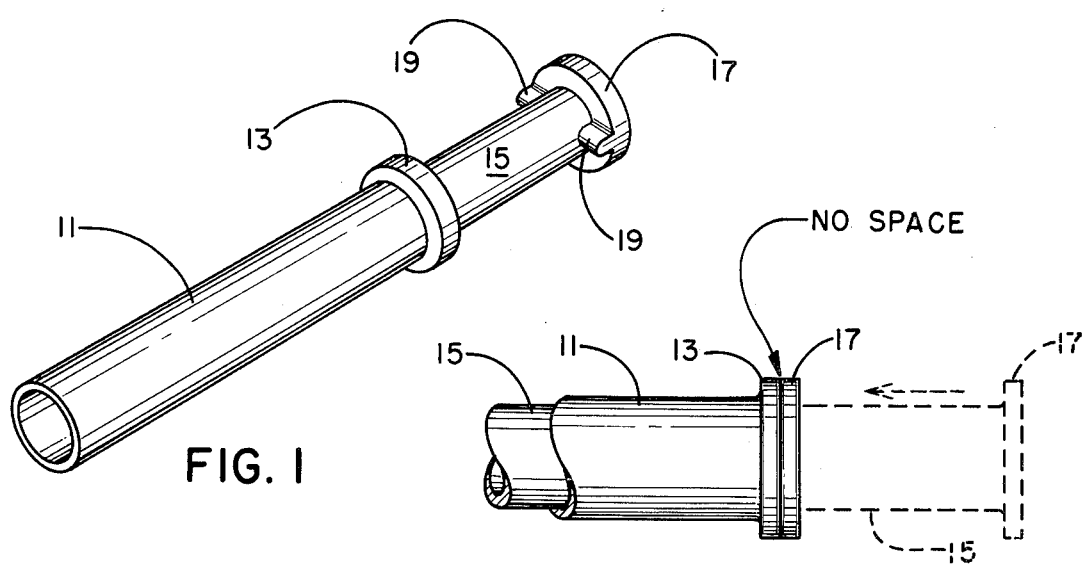
FIG. 1
FIG. 1A (PRIOR ART)
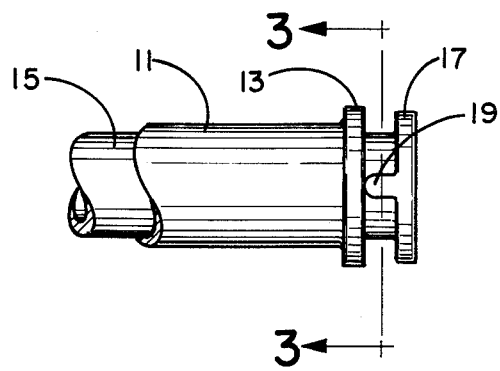
FIG. 2
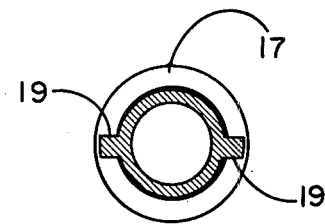
FIG. 3
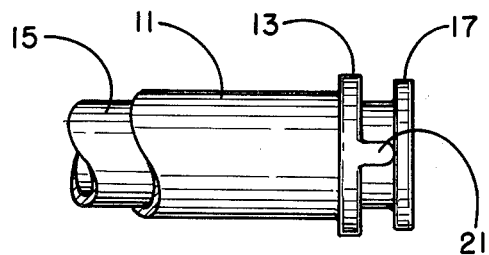
FIG. 4
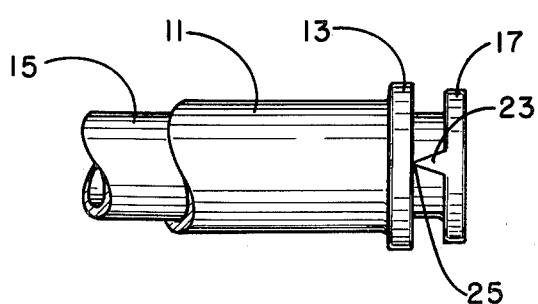
FIG. 5

APPLICATOR FOR INSERTING HYGIENIC MEDIA INTO BODY CAVITIES

BACKGROUND OF THE INVENTION

In the field of applicators used for inserting hygienic media into body cavities, one type of applicator is comprised generally of an outer tube adapted to contain in its forward end the material to be inserted into the body, and an inner plunger slidably disposed in the other end of the tube to eject the material therefrom. In one specific form of such applicators, both the outer tube and inner plunger are provided with annular flanges on the exterior surface of their respective trailing ends. The flange on the outer tube serves primarily as a gripping means, while the flange on the inner plunger serves primarily to regulate the depth or extent to which the plunger can be slid into the outer tube during ejection. While both of these flanges perform their primary functions satisfactorily it has been found that, on occasion, the complete closing and juxtaposition of the confronting flange surfaces which normally takes place during ejection may trap body tissue or hair between the faces of the closed flanges and cause discomfort. The present invention is directed to an improved structure which substantially prevents such undesirable results.

SUMMARY OF THE INVENTION

As indicated above, this invention is directed to an improvement in the structure of a tube-like applicator for hygienic media in which the applicator is comprised of an outer tubular member and an inner plunger telescopically associated therewith, and in which both outer tube and inner plunger are provided with annular flanges at their respective trailing end portions. In such applicators, confronting surfaces of the flanges normally are pushed into contact with each other when the telescoping members are slid together in the insertion and ejection process.

The improvement comprises providing a small, knob-like projection or protuberance on at least one of the confronting flange surfaces which protuberance acts as a stop means and prevents contact of the remaining confronting surface areas of the flanges, which areas would normally be in contact when the tube and plunger are pressed together. In other embodiments, one or both flange faces may be provided with multiple protuberances spaced from each other.

The various aspects of the invention will be more readily understood by reference to the accompanying drawings and detailed description set forth hereinafter.

BRIEF DESCRIPTION OF THE DRAWINGS

In the drawings:

FIG. 1 is a perspective view of one embodiment of an applicator in accordance with the invention.

FIG. 1A is a fragmentary side view of a prior art applicator.

FIG. 2 is a fragmentary side view of the applicator of FIG. 1 with the slidable elements thereof fully telescoped together.

FIG. 3 is a section taken along lines 3—3 of FIG. 2.

FIG. 4 is a fragmentary side view similar to FIG. 2 showing another embodiment of the invention.

FIG. 5 is another fragmentary side view showing still another embodiment of the invention.

DETAILED DESCRIPTION OF THE PREFERRED EMBODIMENTS

Referring to FIGS. 1-3, in which like parts have like members, there is shown an applicator made in accordance with this invention having an outer element of tubular shape and comprised of an open-ended tube 11 having an annular flange 13 disposed around its rear end portion. The front internal portion of the tube is adapted to receive a hygienic medium for insertion into a body cavity. Telescopically associated with outer tube 11 is a tubular plunger 15 with its forward end partially inserted in the rear end of tube 11 and having an annular flange 17 disposed around its rear end portion. Flange 17 has disposed on a part of its forward facing surface which confronts the rearward facing surface of flange 13 a pair of knob-like projections of protuberances 19 diametrically spaced from each other. As shown in FIG. 2, protuberance 19 serves as a stop means, which stop means serves to space the forward facing surface of flange 17 from the rearward facing surface of flange 13 when outer tube 11 and inner plunger 15 are telescoped together. Protuberance 19 thus keeps the confronting surfaces of the flanges from contact and thereby minimizes the possibility of entrapping body tissue or hair between the confronting flange surfaces.

The prior art arrangement is shown in FIG. 1A. In that figure, the phantom lines show the inner plunger 15 partially extended. The solid lines show the elements fully telescoped together with no space between flanges 13 and 17.

In FIG. 4, knob-like protuberance 21 is positioned on the rearward facing surface of flange 13 rather than the forward facing surface of flange 17. In this position, the function of protuberance 21 is similar to that of protuberance 19 shown in FIG. 2, i.e. the confronting flange surfaces are stopped from physically contacting each other when the applicator elements are fully telescoped together.

In FIG. 5, a protuberance 23 is again shown on the rearward facing surface of flange 17 but the shape of the protuberance is different in that it has a pointed extremity 25 which provides a much smaller point of contact between the two flange structures.

While in each of the FIG. 1-3 drawings the knob-like protuberances are indicated as being paired and diametrically opposed on the respective flange it will be understood that the stop function can also be performed when only one protuberance is positioned on either flange or if more than two spaced protuberances are disposed on either one or both flanges.

It will also be understood that the protuberance forming the stop means, can be of a large variety of shapes and sizes, with a small size having minimum points of contact being preferred.

The telescoping elements may also be of various sizes, shapes and configurations with the invention being applicable to any style of telescoping applicators which have confronting faces at their respective rearward portions. The outer tube member may be completely open-ended as shown or may be provided with a flexible closed end of multiple petal shaped elements or the like which are easily caused to open radially when the contents are ejected by the plunger member.

The plunger member may be tubular as shown in the drawings or may have various other configurations as found in the prior art. The important consideration is that some form of stop means be provided on a small area of at least one of the confronting faces of the annular flanges to insure that the faces do not meet when the members are fully telescoped together.

What is claimed is:

1. In an applicator for introducing hygienic media into the vaginal cavity wherein said applicator comprises the combination of an elongated outer tube and a plunger slidably disposed in the rear portion of said tube and in telescopic association therewith, wherein a rear end portion of said tube and a trailing end portion of said plunger each has an annular flange disposed thereabout and wherein when said plunger is slid forward into said tube and said flanges are juxtaposed, the rearward facing surface of the tube flange and the frontward facing surface of the plunger flange comprise confronting faces, and in which said plunger flange alone serves to limit the depth to which the plunger can be slid into the outer tube, the improvement wherein there is provided on only a minor portion of the confronting surface area of one of said faces at least one small discrete projecting element comprising a stop means, the outwardly disposed free end of said element providing the only contact with the other of said faces when said plunger and said tube are fully telescoped together thereby preventing entrapment of body tissue or hair between the remaining portion of the confronting surface area of said faces during use.

2. The applicator of claim 1 wherein said stop means element comprises at least one small knob-like protuberance.

3. The applicator of claim 1 wherein said stop means element is disposed on the confronting face of said plunger flange.

4. The applicator of claim 1 wherein said stop means element is disposed on the confronting face of said tube flange.

5. The applicator of claim 1 wherein said stop means comprises more than one small projecting element spaced about one of said faces.

6. The applicator of claim 5 wherein said stop means is disposed on the confronting face of said plunger flange.

7. The applicator of claim 5 wherein said stop means is disposed on the confronting face of said tube flange.

* * * * *